United States Patent
Yamazaki

(10) Patent No.: US 9,907,517 B2
(45) Date of Patent: Mar. 6, 2018

(54) X-RAY COMPUTED TOMOGRAPHY APPARATUS AND X-RAY DETECTOR

(71) Applicant: Toshiba Medical Systems Corporation, Otawara-shi (JP)

(72) Inventor: Takayuki Yamazaki, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 189 days.

(21) Appl. No.: 15/047,782

(22) Filed: Feb. 19, 2016

(65) Prior Publication Data

US 2016/0242704 A1    Aug. 25, 2016

(30) Foreign Application Priority Data

Feb. 20, 2015  (JP) ................................. 2015-032144
Feb. 3, 2016   (JP) ................................. 2016-019209

(51) Int. Cl.
    *A61B 6/03*   (2006.01)
    *G01T 1/24*   (2006.01)
    *G01T 1/20*   (2006.01)
    *A61B 6/00*   (2006.01)

(52) U.S. Cl.
    CPC ............ *A61B 6/032* (2013.01); *G01T 1/2018* (2013.01); *G01T 1/241* (2013.01); *G01T 1/247* (2013.01); *A61B 6/4233* (2013.01)

(58) Field of Classification Search
    CPC .. A61B 6/00; A61B 6/03; A61B 6/032; A61B 6/54; A61B 6/4233; A61B 6/4266; G01T 1/24; G01T 1/241; G01T 1/247; G01N 23/00; G01N 23/08; G01N 23/083; G01N 23/046; H05G 1/56

USPC ................................ 378/4, 19, 114–116, 901
    See application file for complete search history.

(56) References Cited

U.S. PATENT DOCUMENTS

| | | | |
|---|---|---|---|
| 5,896,173 A * | 4/1999 | Hassler | H04N 5/374 348/162 |
| 2005/0253078 A1 | 11/2005 | Miyazaki et al. | |
| 2009/0080601 A1 | 3/2009 | Tkaczyk et al. | |

FOREIGN PATENT DOCUMENTS

| JP | 2009-78143 | 4/2009 |
|---|---|---|
| JP | 4597171 | 12/2010 |
| JP | 4782902 | 9/2011 |
| JP | 4825443 | 11/2011 |
| JP | 5135423 | 2/2013 |
| JP | 5135424 | 2/2013 |
| JP | 5135425 | 2/2013 |

(Continued)

*Primary Examiner* — Jurie Yun
(74) *Attorney, Agent, or Firm* — Oblon, McClelland, Maier & Neustadt, L.L.P.

(57) ABSTRACT

According to an embodiment, detector cells are provided on a substrate, divided into groups, and detect an X-rays. Switches respectively connected to the detector cells. The data acquisition elements are respectively connected to the groups and configured to integrate electrical signals from a detector cells belonging to each of the groups. The control circuitry are configured to control the switches for each of the groups so as to switch between first connection for substantially simultaneously reading out electrical signals from a detector cells belonging to each of the groups and second connection for reading out electrical signals from a detector cells belonging to each of the groups at different timings.

13 Claims, 13 Drawing Sheets

(56) References Cited

FOREIGN PATENT DOCUMENTS

WO      WO 98/24059  A1    6/1998

* cited by examiner

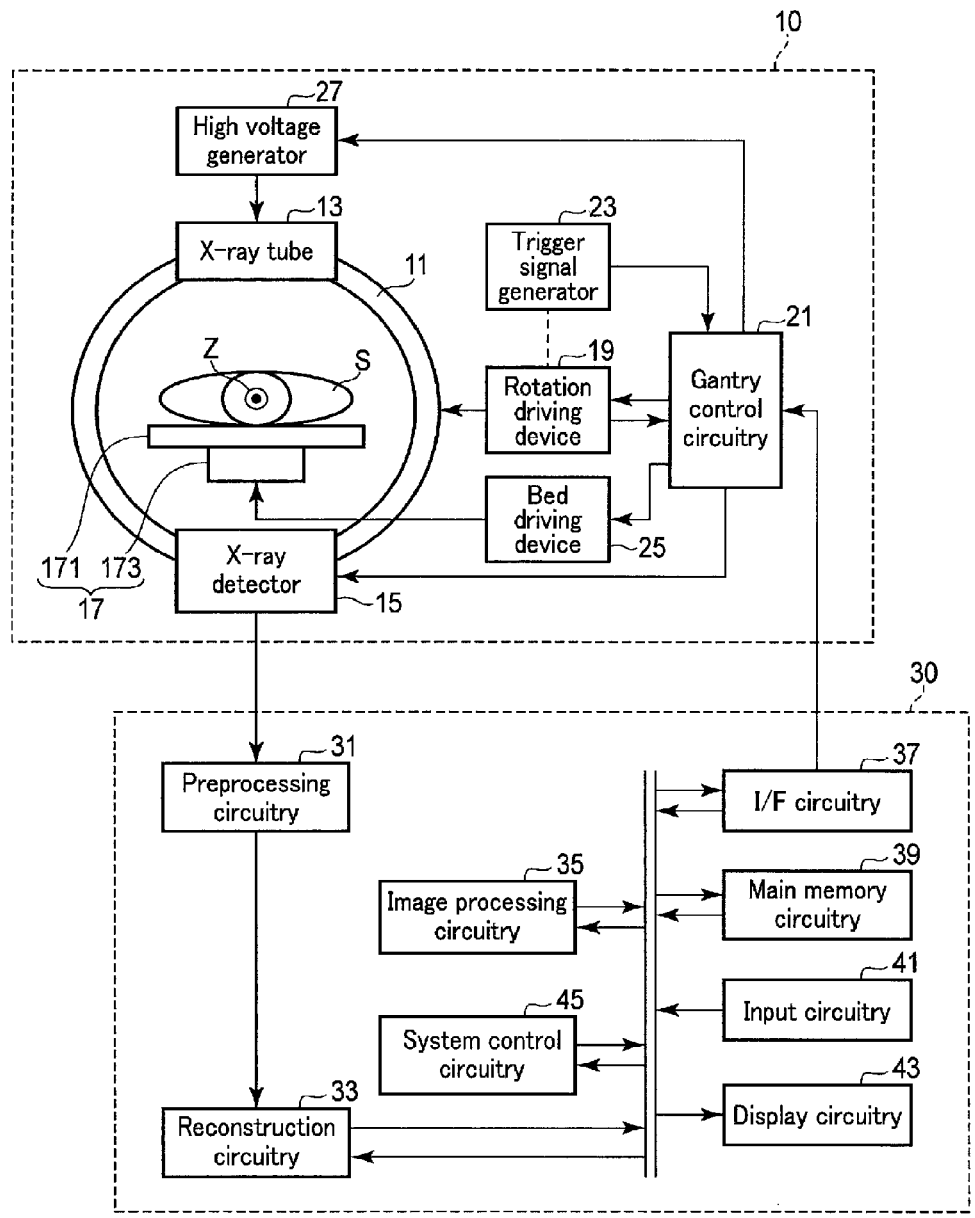
F I G. 1

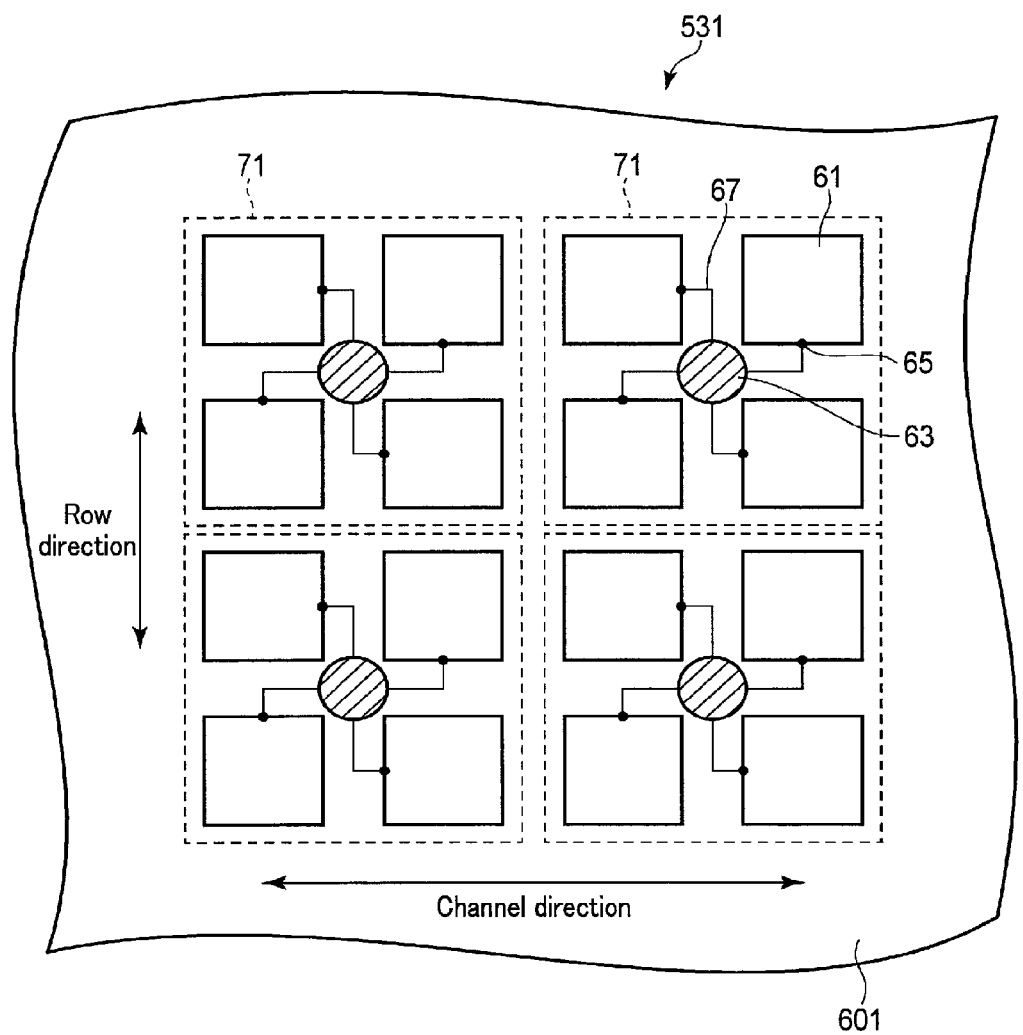
F I G. 4

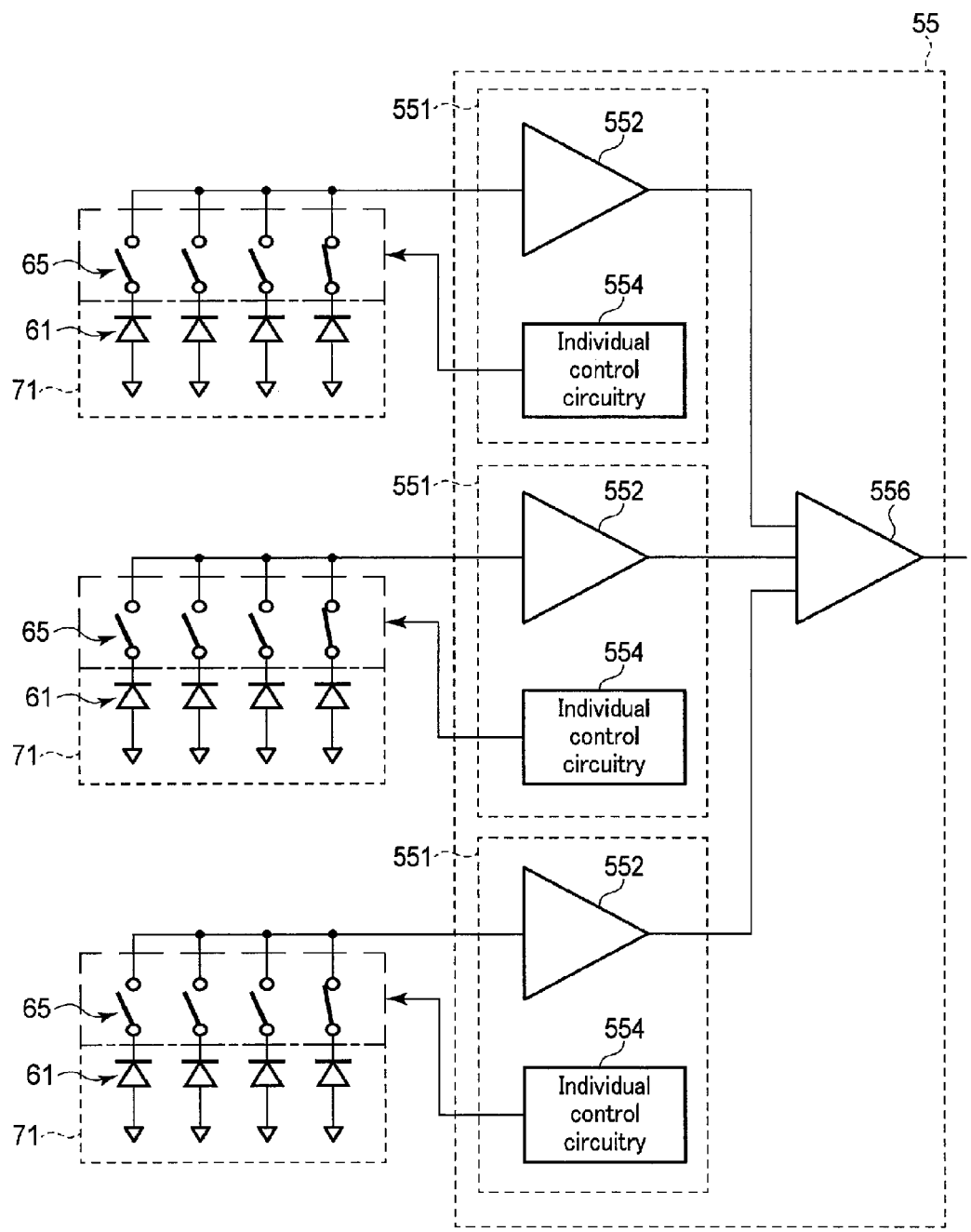
F I G. 5

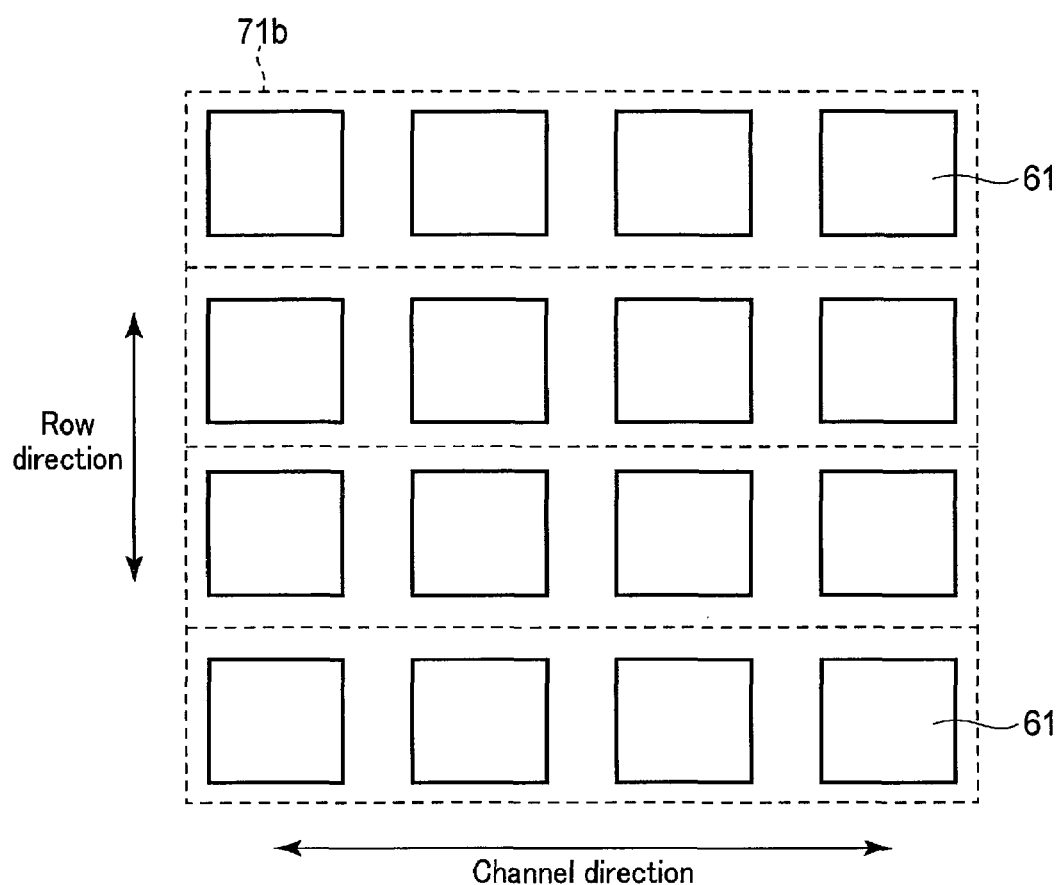
F I G. 12

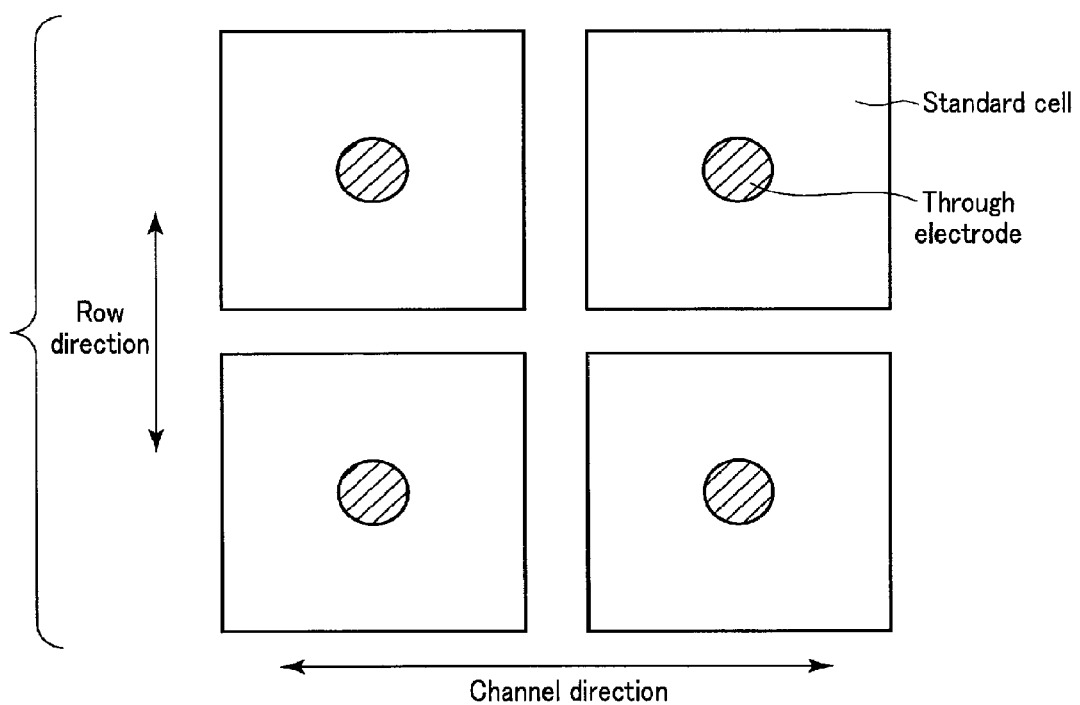
Related art
(standard cell by simultaneous readout)
F I G. 13

X-RAY COMPUTED TOMOGRAPHY APPARATUS AND X-RAY DETECTOR

CROSS-REFERENCE TO RELATED APPLICATIONS

This application is based upon and claims the benefit of priority from the prior Japanese Patent Application No. 2015-032144, filed Feb. 20, 2015 and Japanese Patent Application No. 2016-019209, filed Feb. 3, 2016, the entire contents of all of which are incorporated herein by reference.

FIELD

Embodiments described herein relate generally to an X-ray computed tomography apparatus and an X-ray detector.

BACKGROUND

An X-ray computed tomography apparatus includes an X-ray detector which detects X-rays. The X-ray detector includes a plurality of detector cells which detect X-rays and a plurality of DAS (Data Acquisition System) elements which process electrical signals from the respective detector cells. More specifically, the DAS elements read out electrical signals from the detector cells, integrate the readout electrical signals, and convert the integral signal into digital data.

A high-resolution detector has also been developed, which has an array of a plurality of detector cells, each having a size smaller than a standard size, to acquire data with a high resolution. As schemes of reading out electrical signals from detector cells, a simultaneous readout scheme and a sequential readout scheme are known. In the simultaneous readout scheme, a plurality of detector cells are connected one-to-one to a plurality of DAS elements. The simultaneous readout scheme can achieve simultaneity in terms of integration time between detector cells and high-speed readout of electrical signals, but is technically difficult to be implemented in a high-resolution detector because of high-density signal wiring lines between detector cells and DAS elements. In addition, in the simultaneous readout scheme, although detector cells are directly connected to DAS elements via through electrodes, the contact area of each through electrode to a corresponding detector cell occupies a large part of the cell area. This makes it difficult to reduce the cell size. In the sequential readout scheme, a plurality of detector cells are connected to DAS elements via common signal wiring lines. For this reason, the sequential readout scheme allows a reduction in cell size more easily than the simultaneous readout scheme. In addition, in the sequential readout scheme, because of the above wiring scheme, the density of signal wiring lines between detector cells and DAS elements does not become high even when using a high-resolution detector, but simultaneity in terms of integration time between the detector cells collapses.

BRIEF DESCRIPTION OF THE DRAWING

FIG. 1 is a block diagram showing the arrangement of an X-ray computed tomography apparatus according to an embodiment;

FIG. 4 is a plan view schematically showing a plurality of detector cells mounted on a detector cell chip according to this embodiment;

FIG. 5 is a circuit diagram showing the detailed arrangement of an X-ray detector in FIG. 1;

FIG. 12 is a view showing still another example of a cell group according to this embodiment;

FIG. 13 is a plan view schematically showing the structure of an X-ray detector (simultaneous readout scheme and standard cells) according to a related art;

DETAILED DESCRIPTION

Figure 2:
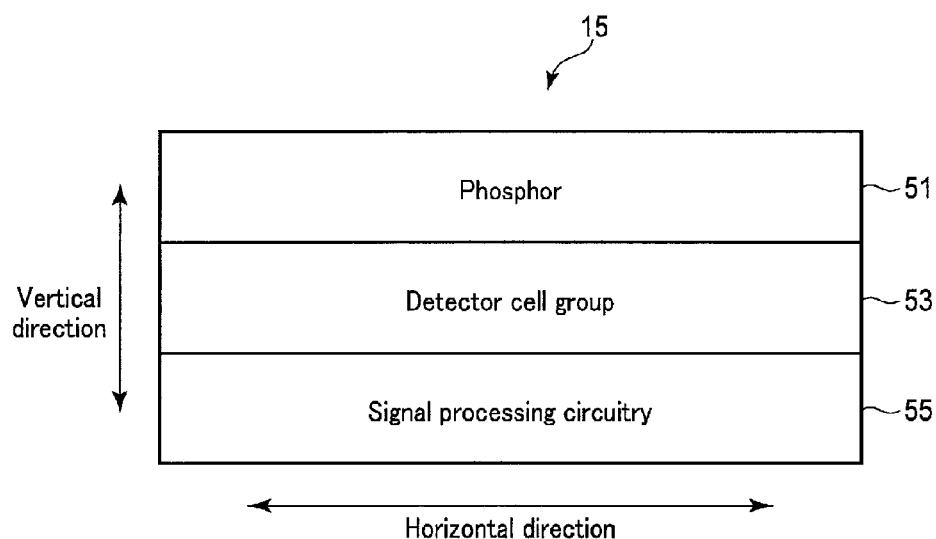
FIG. 2 is a view schematically showing the arrangement of an X-ray detector in FIG. 1.

In general, according to one embodiment, an X-ray computed tomography apparatus includes an X-ray tube, a plurality of detector cells, a plurality of switches, a plurality of data acquisition elements, a control circuitry and a reconstruction circuitry. The X-ray tube is configured to generate X-rays. The plurality of detector cells are provided on a substrate, divided into a plurality of groups, and configured to detect the X-rays. The plurality of switches are respectively connected to the plurality of detector cells The plurality of data acquisition elements are respectively connected to the plurality of groups and configured to integrate electrical signals from a plurality of detector cells belonging to each of the groups. The control circuitry are configured to control the plurality of switches for each of the groups so as to switch between first connection for substantially simultaneously reading out electrical signals from a plurality of detector cells belonging to each of the groups and second connection for reading out electrical signals from a plurality of detector cells belonging to each of the groups at different timings. The reconstruction circuitry are configured to reconstruct an image based on outputs from the plurality of data acquisition elements.

An X-ray computed tomography apparatus and an X-ray detector according to this embodiment will be described below with reference to the accompanying drawing.

FIG. 1 is a block diagram showing the arrangement of an X-ray computed tomography apparatus according to this embodiment. As shown in FIG. 1, an X-ray computed tomography apparatus 1 includes a gantry 10 and a console 30.

The gantry 10 supports a rotating frame 11 having a cylindrical shape so as to allow it to be rotatable around a rotation axis Z. An X-ray tube 13 and an X-ray detector 15 are mounted on the rotating frame 11 so as to face each other through the rotation axis Z. An FOV (Field Of View) is set in the bore of the rotating frame 11. A bed 17 is inserted into the bore of the rotating frame 11. A subject S is placed on the bed 17. The rotating frame 11 receives motive power from a rotation driving device 19 and rotates around the rotation axis Z at a predetermined angular velocity. The rotation driving device 19 is implemented by a motor which generates motive power for rotating the rotating frame 11 in accordance with a control signal from a gantry control circuitry 21. A trigger signal generator 23 is mounted on the rotation driving device 19. The trigger signal generator 23 includes a rotary encoder connected to the drive shaft of the motor which is a bed driving device 25. The trigger signal generator 23 repeatedly generates electrical pulse signals (to be referred to as view trigger signals hereinafter) every time the rotating frame 11 rotates through a predetermined angle. View trigger signals are supplied to the gantry control circuitry 21. A unit time between view trigger signals is called a view.

The bed 17 includes a top 171 on which the subject S is placed and a top support base 173 which movably supports the top 171. For example, the top support base 173 supports the top 171 so as to allow it to be movable in the rotation axis Z direction, the vertical direction, and the horizontal direction. The top support base 173 receives motive power from the bed driving device 25 and moves the top 171 in an arbitrary direction. The bed driving device 25 is implemented by a motor which moves the top 171 in an arbitrary direction under the control of the gantry control circuitry 21. The bed driving device 25 is accommodated in, for example, the top support base 173.

The X-ray tube 13 receives a high voltage and filament current from a high voltage generator 27, and generates X-rays. The high voltage generator 27 applies a high voltage to the X-ray tube 13 and supplies a filament current to it in accordance with control signals from the gantry control circuitry 21.

The X-ray detector 15 detects X-rays generated from the X-ray tube 13, and generates a digital signal (to be referred to as raw data hereinafter) having a digital value corresponding to the intensity of the detected X-rays.

FIG. 2 is a view schematically showing the main arrangement of the X-ray detector 15. As shown in FIG. 2, the X-ray detector 15 includes a phosphor 51, a cell group 53, and a signal processing circuitry 55 which are stacked in one direction. The stacking direction of the phosphor 51, the cell group 53, and the signal processing circuitry 55 will be referred to as the vertical direction, and a direction perpendicular to the vertical direction will be referred to as the horizontal direction hereinafter. The phosphor 51 is placed on the surface of the X-ray detector 15. The phosphor 51 is a luminescent material (scintillator) which absorbs X-rays and emits fluorescence having a light amount corresponding to the intensity of the absorbed X-rays. The cell group 53 is provided on the back surface of the phosphor 51.

Figure 3:
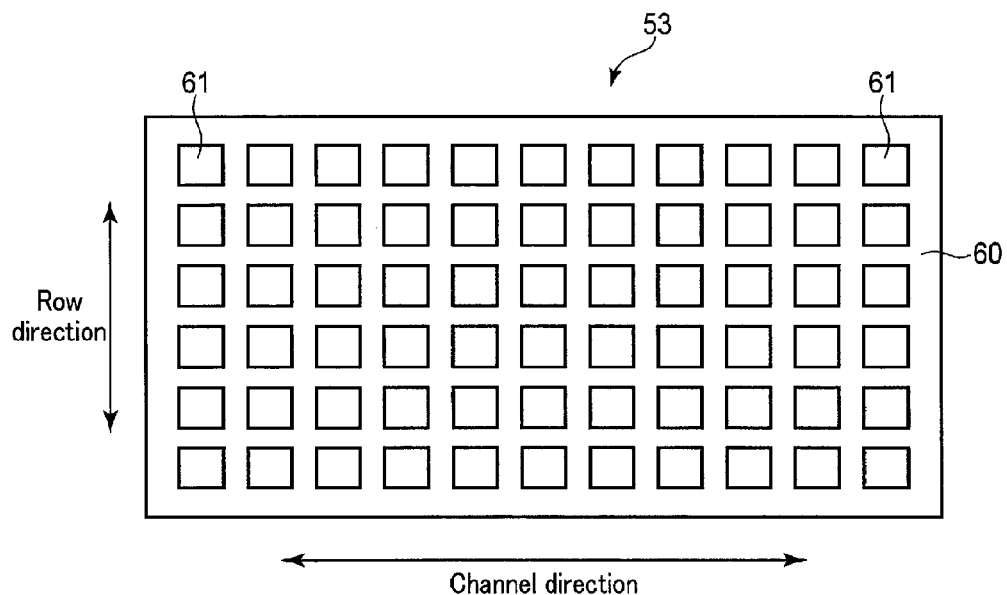
FIG. 3 is a view schematically showing the structure of a detector cell group in FIG. 2.

FIG. 3 is a schematic view showing the structure of the cell group 53. As shown in FIG. 3, the cell group 53 includes a plurality of detector cells 61 arrayed two-dimensionally. Of the two directions defining the array surface of the detector cells 61, a direction parallel to the rotation axis Z will be referred to as a row direction, and a direction perpendicular to the row direction will be referred to as a channel direction. The plurality of detector cells 61 are formed on the front or back surface of a semiconductor substrate 60. Each detector cell 61 receives fluorescence propagating from the phosphor 51, and converts the fluorescence into an electrical signal having a peak value corresponding to the light amount of received fluorescence. That is, each detector cell 61 indirectly detects X-rays converted into light. More specifically, each detector cell 61 includes a photodiode having electrodes attached to the two ends of a semiconductor. X-rays entering the semiconductor are converted into electron-hole pairs. Electrons and holes are attracted to a pair of anode and cathode respectively formed on the two ends of the semiconductor to generate an electrical pulse having a peak value corresponding to the charges of electron/hole pairs. One electrical pulse has a peak value corresponding to the intensity of incident X-rays.

As shown in FIG. 2, the signal processing circuitry 55 is provided on the back surface of the cell group 53. The signal processing circuitry 55 includes a plurality of integrated circuits (to be referred to as DAS elements hereinafter) for processing electrical signals from the plurality of detector cells 61. Each DAS element is connected to a plurality of detector cells 61 via signal wiring lines. Each DAS element reads out electrical signals from the detector cells 61 as connection sources, generates an integral signal of the readout electrical signals, and converts the integral signal into raw data having a digital value corresponding to the peak value of the integral signal. A noncontact data transmitter or the like transmits the raw data to the console 30.

Note that in the above description, the X-ray detector 15 is of an indirect detection type that indirectly detects X-rays by converting X-rays into light. However, this embodiment is not limited to this. For example, the X-ray detector 15 may be of a direct detection type that directly detects X-rays. In this case, the phosphor 51 is not provided on the back surface of the cell group 53, and each detector cell 61 directly detects X-rays.

As shown in FIG. 1, the gantry control circuitry 21 comprehensively controls various types of devices mounted on the gantry 10. The gantry control circuitry 21 includes, as hardware resources, an arithmetic device (processor) such as a CPU (Central Processing Unit) or MPU (Micro Processing Unit) and storage devices (memories) such as a ROM (Read Only Memory) and a RAM (Random Access Memory). The gantry control circuitry 21 is accommodated in the gantry 10. In particular, the gantry control circuitry 21 synchronously controls the X-ray detector 15, the rotation driving device 19, and the high voltage generator 27. More specifically, the gantry control circuitry 21 controls the rotation driving device 19 so as to rotate the rotating frame 11 at a predetermined angular velocity. The gantry control circuitry 21 synchronously controls a DAS 153 and the high voltage generator 27 in synchronism with the supply of a view trigger signal from the trigger signal generator 23. The high voltage generator 27 causes the X-ray tube 13 to generate X-rays under the control of the gantry control circuitry 21. The DAS 153 acquires raw data via the X-ray detector 15 under the control of the gantry control circuitry 21. In addition, the gantry control circuitry 21 controls the bed driving device 25 so as to move the top 171 in accordance with an input from the user via input circuitry 41 (to be described later). For example, the gantry control circuitry 21 controls the bed driving device 25 so as to position the top 171 such that an imaging region of the subject S is included in an FOV. Note that the high voltage generator 27 may continuously generate X-rays during a data acquisition period.

The console 30 includes preprocessing circuitry 31, reconstruction circuitry 33, image processing circuitry 35, I/F circuitry 37, main memory circuitry 39, the input circuitry 41, display circuitry 43, and system control circuitry 45.

The preprocessing circuitry 31 includes, as hardware resources, an arithmetic device such as a GPU (Graphics Processing Unit) and storage devices such as a ROM and a RAM. The preprocessing circuitry 31 performs preprocessing such as logarithmic conversion for raw data transmitted from the gantry 10. Raw data after preprocessing is also called projection data. Preprocessing includes various types of correction processing such as logarithmic conversion, X-ray intensity correction, and offset correction.

The reconstruction circuitry 33 includes, as hardware resources, an arithmetic device such as a CPU, MPU, or GPU and storage devices such as a ROM and a RAM. The reconstruction circuitry 33 generates a CT image expressing the spatial distribution of CT values concerning the subject S based on raw data after preprocessing. As an image reconstruction algorithm, there may be used an existing image reconstruction algorithm such as an analytical image reconstruction method such as an FBP (Filtered Back Projection) method or CBP (Convolution Back Projection) method or a statistical image reconstruction method such as an ML-EM (Maximum Likelihood Expectation Maximization) method or OS-EM (Ordered Subset Expectation Maximization) method.

Note that the preprocessing circuitry 31 and the reconstruction circuitry 33 may be incorporated in a single hardware resource.

The image processing circuitry 35 includes, as hardware resources, an arithmetic device such as a CPU, MPU, or GPU and storage devices such as a ROM and a RAM. The image processing circuitry 35 performs various types of image processing for a CT image reconstructed by the reconstruction circuitry 33. For example, the image processing circuitry 35 generates a display image by performing three-dimensional image processing such as volume rendering, surface volume rendering, image value projection processing, MPR (Multi-Planner Reconstruction) processing, or CPR (Curved MPR) processing.

The I/F circuitry 37 is an interface for communication between the console 30 and the gantry 10. For example, the I/F circuitry 37 transmits preset imaging conditions to the gantry 10.

The main memory circuitry 39 is a storage device such as an HDD (Hard Disk Drive) which stores various types of information. For example, the main memory circuitry 39 stores CT image and display image data. Also, the main memory circuitry 39 stores control programs and the like according to this embodiment.

The input circuitry 41 accepts various types of commands and information inputs from the user of an input device. As the input device, a keyboard, a mouse, various types of switches, and the like can be used.

The display circuitry 43 displays setting screens for CT images and scan planning and the like. As the display unit, for example, a CRT display, liquid crystal display, organic EL display, plasma display, or the like can be used as needed.

The system control circuitry 45 includes, as hardware resources, an arithmetic device such as a CPU or MPU and storage devices such as a ROM and a RAM. The system control circuitry 45 functions as the main unit of the X-ray computed tomography apparatus 1. More specifically, the system control circuitry 45 reads out a control program stored in the main memory circuitry 39 and loads it in the memory. The system control circuitry 45 then controls the respective units of the X-ray computed tomography apparatus in accordance with the loaded control program.

The details of the X-ray detector and the X-ray computed tomography apparatus according to this embodiment will be described next.

The structure and operation of the X-ray detector according to a related art will be described first. FIG. 13 is a plan view schematically showing the structure of the X-ray detector according to the related art. The X-ray detector shown in FIG. 13 includes detector cells each having a standard cell size, and adopts the simultaneous readout scheme. A plurality of detector cells are two-dimensionally arrayed on a semiconductor substrate. A detector cell having a standard cell size is sometimes called a standard cell. A through electrode is provided in the back surface of each detector cell. In the back surface of the semiconductor substrate, the through electrodes are connected to DAS elements (not shown). In this manner, the standard cells are one-to-one connected to the DAS elements via through electrodes. Simultaneous readout is performed by almost simultaneously reading out electrical signals from a plurality of standard cells for each view. When the standard cells are one-to-one connected to the DAS elements via the through electrodes in this manner, since the contact area of each through electrode to a corresponding standard cell does not occupy a large part of the cell size of the standard cell, it is possible to ensure effective cell areas. However, since this X-ray detector is formed from the standard cells, the detector cannot acquire data with a high resolution.

Figure 14:
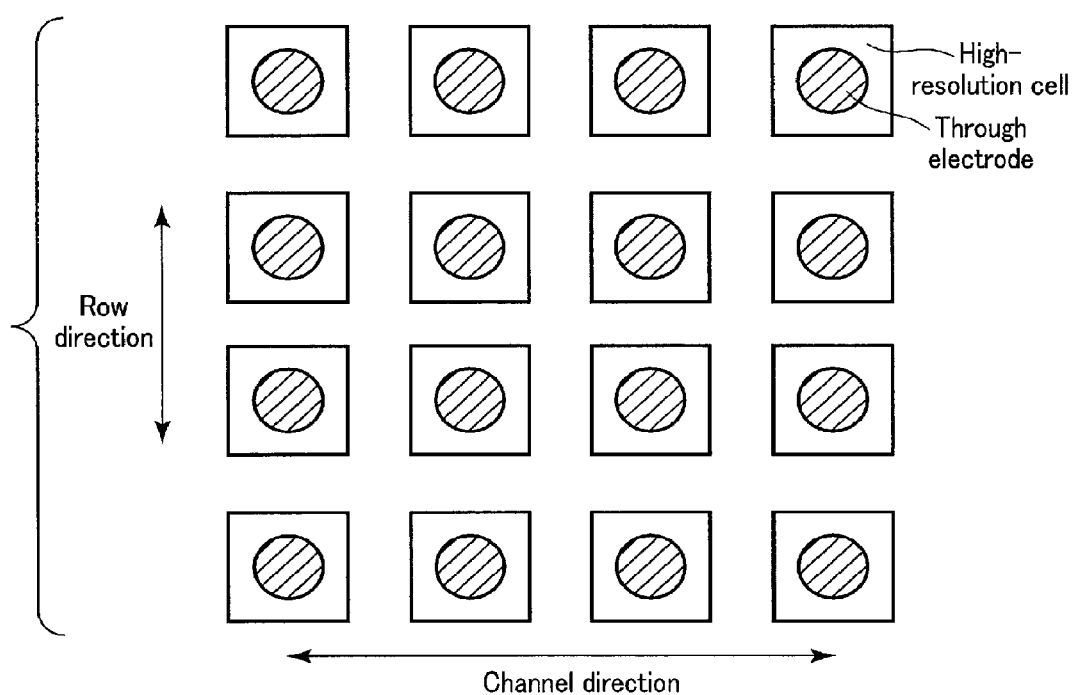
FIG. 14 is a plan view schematically showing the structure of an X-ray detector (simultaneous readout scheme and high-resolution cells) according to a related art.

FIG. 14 is a plan view schematically showing the structure of another X-ray detector according to a related art. The X-ray detector shown in FIG. 14 includes detector cells each having a high-resolution cell size, and adopts the simultaneous readout scheme. In the following description, each detector cell having a high-resolution cell size is sometimes called a high-resolution cell. As shown in FIG. 14, when high-resolution cells are one-to-one connected to DAS elements via through electrodes, like standard cells, since the contact area of each through electrode to a corresponding standard cell occupies a large part of the cell size of the high-resolution cell, it is not possible to ensure effective cell areas. In addition, when high-resolution cells are one-to-one connected to DAS elements, signal wiring lines have a high density, resulting in technical difficulty in implementation. It is also difficult to form DAS elements and high-resolution cells with similar sizes.

Figure 15:
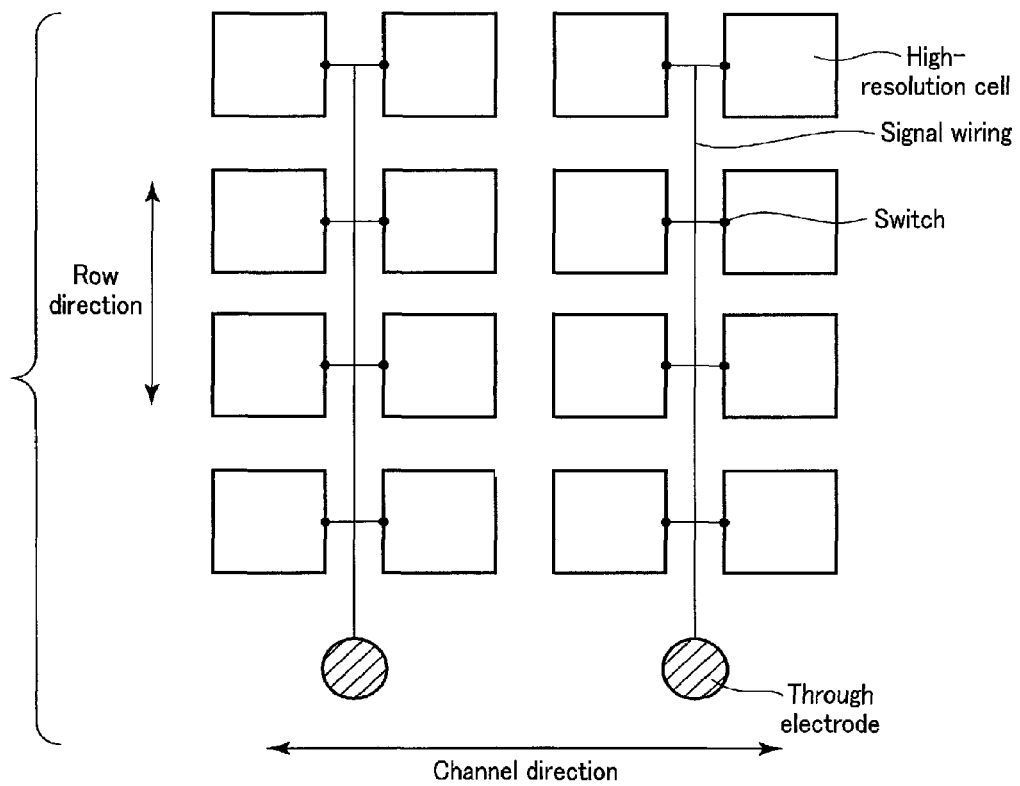
FIG. 15 is a plan view schematically showing the structure of an X-ray detector (sequential readout scheme and high-resolution cells) according to a related art.

FIG. 15 is a plan view schematically showing the structure of still another X-ray detector according to a related art. The X-ray detector shown in FIG. 15 includes high-resolution cells, and adopts the sequential readout scheme. As shown in FIG. 15, when adopting the sequential readout scheme, through electrodes or bonding pads are provided around the implementation range of a plurality of high-resolution cells on a semiconductor substrate. A switch is connected to each high-resolution cell. A plurality of high-resolution cells share through electrodes or bonding pads on a column basis, and are connected to the through electrodes or bonding pads via signal wiring lines. In the sequential readout scheme, since the back surface of each high-resolution cell is not connected to a through electrode, it is possible to ensure effective cell areas for the high-resolution cells. Sequential readout is performed by reading out electrical signals from high-resolution cells at different timings for each view. However, simultaneity in terms of integration time between a plurality of high-resolution cells connected to a common signal wiring line collapses.

The X-ray detector 15 according to this embodiment has an arrangement capable of both data acquisition with a standard resolution and data acquisition with high resolution. The X-ray detector 15 according to the embodiment will be described in detail below.

As described above, the X-ray detector 15 includes the phosphor 51, the cell group 53 including the plurality of detector cells 61, and the signal processing circuitry 55 including the plurality of DAS elements. The cell group 53 includes a plurality of semiconductor chips (to be referred to as detector cell chips hereinafter) on which the plurality of detector cells 61 are formed by a semiconductor process. The signal processing circuitry 55 includes a plurality of semiconductor chips (to be referred to as DAS chips hereinafter) on which a plurality of DAS elements are formed by a semiconductor process.

The plurality of detector cell chips and the plurality of DAS chips are arrayed on an insulating substrate (not shown) such as a printed board two-dimensionally in the row direction and the channel direction.

FIG. 4 is a schematic plan view of the plurality of detector cells 61 mounted on a detector cell chip 531 according to this embodiment. FIG. 4 is a view when the cell group 53 is seen from the X-ray tube 13 side. As shown in FIG. 4, the plurality of detector cells 61 are two-dimensionally arrayed on a semiconductor substrate 601. The semiconductor substrate 601 may be the semiconductor substrate of the detector cell chip 531 or the semiconductor substrate of the DAS chip. As the detector cells 61 according to this embodiment, either high-resolution cells or standard cells may be used. However, this embodiment will exemplify the detector cells 61 as high-resolution cells for the improvement of the utility of the X-ray detector 15 according to the embodiment. In addition, both the numbers of cells in the column and channel directions are four in FIG. 4. However, this is not exhaustive, and the number of cells can be any number. Furthermore, the embodiment is not limited to a case in which the number of cells in the row direction is equal to that in the channel direction. These numbers of cells may differ from each other.

As shown in FIG. 4, a plurality of through electrodes 63 are formed between the plurality of detector cells 61. Each through electrode 63 is formed by forming a metal film on the inner circumferential surface of a through hole formed in the semiconductor substrate 601. The number of through electrodes 63 included in the X-ray detector 15 is smaller than that of detector cells 61. As described above, the through electrodes 63 of the X-ray detector 15 according to this embodiment are provided at positions other than positions on the back surfaces of the detector cells 61, unlike as shown in FIG. 14, and positions outside the implementation range of the detector cells 61, unlike as shown in FIG. 15. Each detector cell 61 is provided with a switch 65 which turns on/off the mode of reading out an electrical signal stored in the detector cell 61. Each switch 65 operates in synchronism with a control signal from a control circuitry (to be described later). Each detector cell 61 is connected to the through electrode 63 via the switch 65 and a signal wiring line 67. The signal wiring line 67 is formed from a conductive material such as aluminum or copper. Note that a signal wiring line which connects the switch 65 to a control circuitry which controls the switch 65 is provided separately from the signal wiring line 67 which connects the detector cell 61 to the through electrode 63. However, for the sake of simplicity, a description of such signal wiring lines will be omitted.

As shown in FIG. 4, the plurality of detector cells 61 are divided into a plurality of groups 71 smaller in number than the detector cells 61. These groups will be referred to as cell groups 71.

For example, referring to FIG. 4, adjacent four cells are formed into one cell group 71. The number of detector cells 61 included in the cell group 71, the number of cells in the channel direction, and the number of cells in the row direction can be arbitrarily set. For example, referring to FIG. 4, two cells in the row direction and two cells in the channel direction constitute one cell group 71. One through electrode 63 is assigned to each cell group 71. The plurality of detector cells 61 belonging to each cell group 71 are connected to the corresponding through electrode 63 and, more specifically, are connected to the plurality of switches 65 via the signal wiring lines 67. In other words, a plurality of detector cells 61 are bundled into one cell group 71. Each through electrode 63 is formed, in the semiconductor substrate 601, at an arbitrary portion of a portion (lattice-like portion) where the four detector cells 61 belonging to the corresponding cell group 71 are not formed. For example, the through electrode 63 is formed at almost the center of the four detector cells 61 belonging to each cell group 71. This makes it possible to equalize the distances between the through electrode 63 and the respective detector cells 61. This can improve simultaneity in term of integration time.

In the X-ray detector 15 according to this embodiment, when acquiring data with a standard resolution, each cell group 71 is regarded as standard cells, and electrical signals are almost simultaneously read out from the high-resolution cells 61 belonging to the cell group 71. When acquiring data with a high resolution, each cell group 71 is regarded as a unit of readout, and electrical signals are read out from the plurality of high-resolution cells 61 belonging to the cell group 71 at different timings. In the following description, a control mode of acquiring data with a standard resolution will be referred to as a standard cell mode, and a control mode of acquiring data with a high resolution will be referred to as a high-resolution cell mode.

The detailed arrangement and operation of the X-ray detector 15 according to this embodiment will be described below.

FIG. 5 is a circuit diagram showing the detailed arrangement of the X-ray detector 15 according to this embodiment. As shown in FIG. 5, the X-ray detector 15 according to the embodiment includes the plurality of cell groups 71 and the signal processing circuitry 55. The signal processing circuitry 55 includes a plurality of DAS elements 551 and an A/D converter 556.

As shown in FIG. 5, the DAS elements 551 are respectively connected to the plurality of cell groups 71. Each cell group 71 includes the plurality of detector cells 61. The switch 65 is connected to each of the plurality of detector cells 61. The plurality of switches 65 belonging to each cell group 71 are connected to the DAS element 551 via a common signal line.

Each DAS element 551 includes, for example, an integration circuit 552 and an individual control circuit 554. Each integration circuit 552 reads out electrical signals from the plurality of detector cells 61 belonging to the corresponding cell group 71 as the connection source via the plurality of switches 65, and integrates the readout electrical signals over a predetermined period. The predetermined period is set in accordance with the period of one view. Each individual control circuit 554 controls connection and disconnection of the plurality of switches 65 belonging to the corresponding cell group 71 as a connection source. More specifically, the individual control circuit 554 individually controls the plurality of switches 65 to switch the connection between the plurality of switches 65 belonging to the cell group 71 as the connection source and the integration circuit 552 between connection for the standard cell mode and connection for the high-resolution mode. In the standard cell mode, each individual control circuit 554 almost simultaneously reads out electrical signals from the plurality of detector cells 61 belonging to the corresponding cell group 71 as a connection source by almost simultaneously opening/closing all the plurality of switches 65 belonging to the cell group 71 as the connection source. In the high-resolution cell mode, each individual control circuit 554 reads out electrical signals from the plurality of detector cells 61 belonging to the corresponding cell group 71 as a connection source at different timings by opening/closing the plurality of switches 65 belonging to the cell group 71 as the connection source at different timings.

As shown in FIG. 5, the A/D converter 556 is connected to the plurality of DAS elements 551, and generates raw data by A/D-converting an integral signal from the plurality of DAS elements 551. The number of DAS elements 551 connected to the A/D converter 556 is arbitrary. Typically, one A/D converter 556 is connected to a predetermined number of DAS elements 551. However, this embodiment is not limited to this. One A/D converter 556 may be connected to one DAS element 551. In this case, the A/D converter 556 is provided for each DAS element 551.

Figure 6:
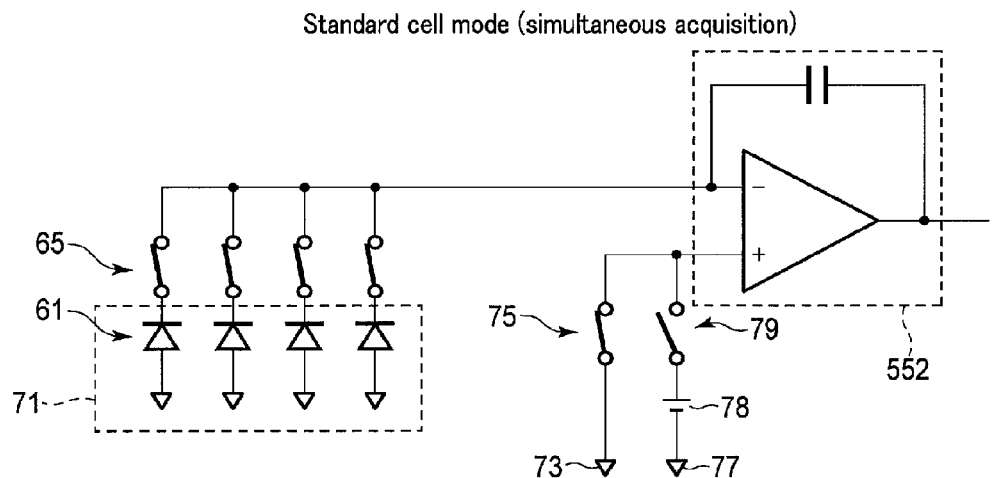
FIG. 6 is a circuit diagram for explaining electrical signal readout in a standard cell mode according to this embodiment.

FIG. 6 is a circuit diagram for explaining electrical signal readout in the standard cell mode. FIG. 6 shows only the circuit of only one cell group 71. As shown in FIG. 6, the switch 65 is connected to each detector cell 61. The switches 65 belonging to each cell group 71 are connected in parallel to the negative pole of the DAS element (more specifically, an integration circuit) 552. A ground (GND) 73 is connected to the positive pole of the integration circuit 552 via a switch 75. A bias power supply 78 connected to a ground 77 is connected to the positive pole of the integration circuit 552 via a switch 79. In the standard cell mode, the switch 79 is opened to disconnect the integration circuit 552 from the bias power supply 78, and the switch 75 is closed to connect the integration circuit 552 to the ground 73, thereby setting each detector cell in a non-bias state. In the simultaneous readout mode, while the connection between the integration circuit 552 and the ground 73 is maintained, the connection of all the switches 65 belonging to the cell group 71 is always closed, thereby performing simultaneous readout.

Figure 7:
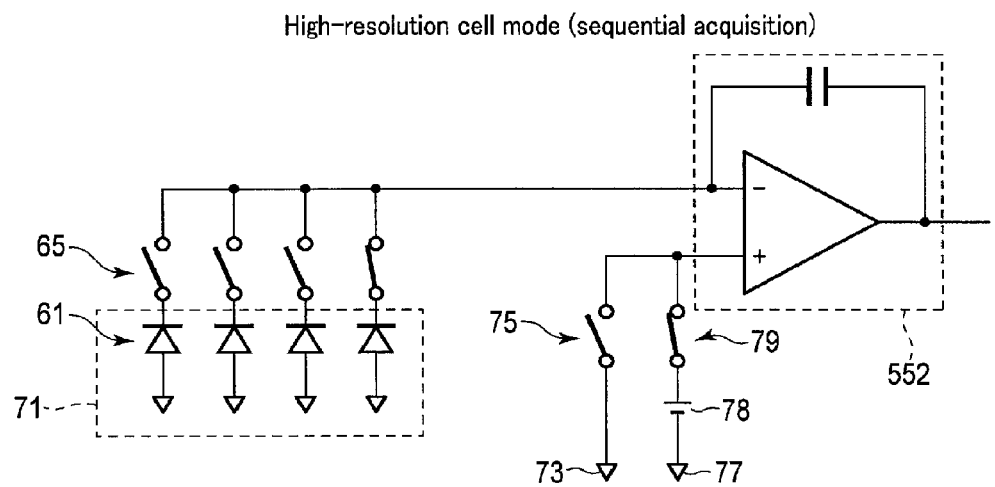
FIG. 7 is a circuit diagram for explaining electrical signal readout in a high-resolution cell mode according to this embodiment.

FIG. 7 is a circuit diagram for explaining electrical signal readout in the high-resolution cell mode. Like FIG. 6, FIG. 7 shows the circuit of only one cell group 71. In the high-resolution cell mode, the switch 79 is closed to connect the integration circuit 552 to the bias power supply 78 to apply a bias voltage to each detector cell 61. The switch 75 is opened to disconnect the integration circuit 552 from the ground 73. Electric charge corresponding to an input is accumulated in each detector cell corresponding to the switch 65 in the OFF state. While the connection between the integration circuit 552 and the bias power supply 78 is maintained, the plurality of switches 65 are sequentially turned on to read out accumulated electric charges to the integration circuit 552. With this operation, sequential readout is performed.

A control system for the switches 65 of the X-ray detector 15 according to this embodiment will be described next.

Figure 8:
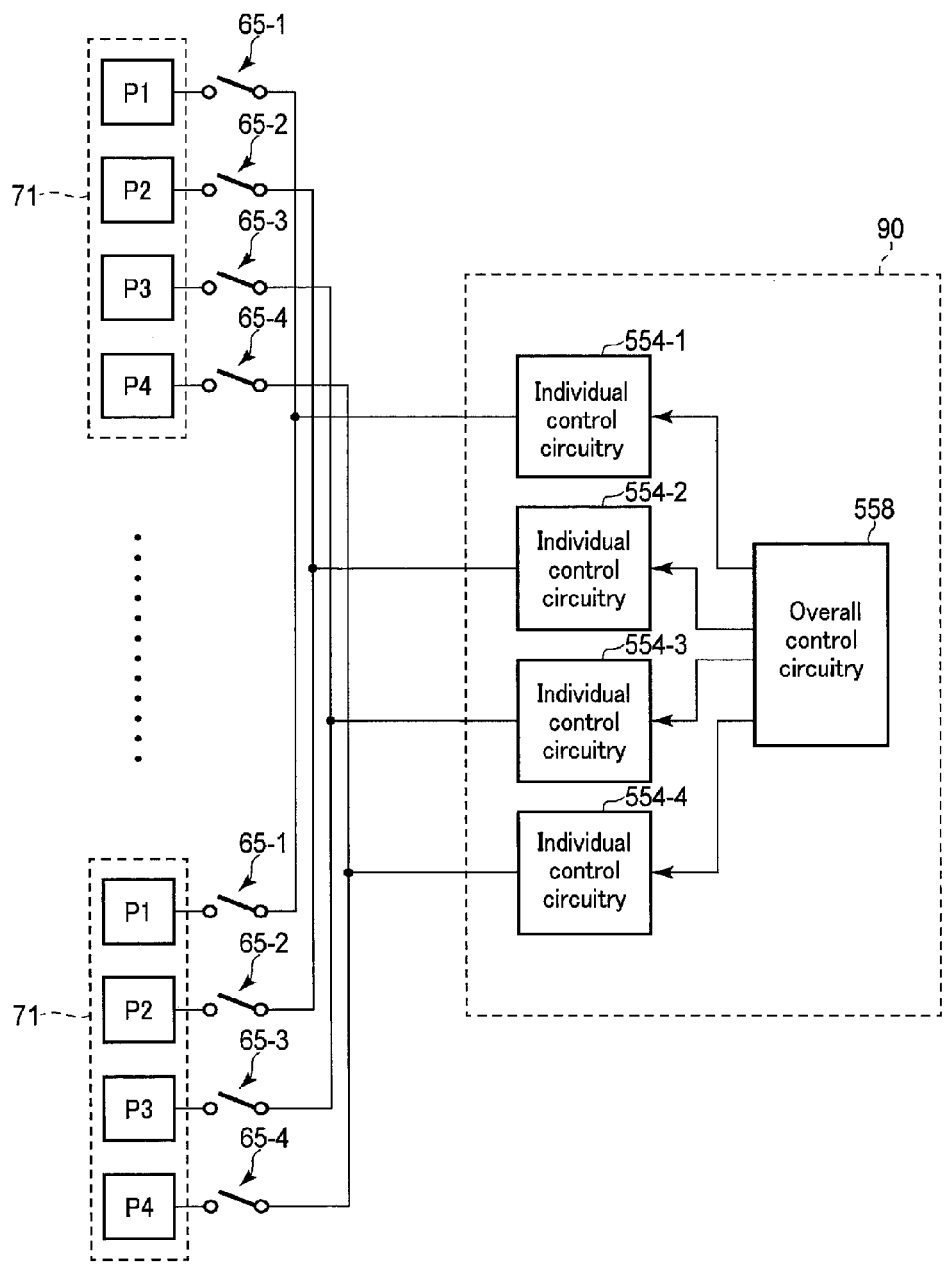
FIG. 8 is a block diagram showing a control system for the switches of an X-ray detector according to this embodiment.

FIG. 8 is a circuit diagram showing the control system for the switches 65 of the X-ray detector 15 according to this embodiment. As shown in FIG. 8, the plurality of detector cells 61 are arrayed on the semiconductor substrate 601, and a switch is connected to each detector cell. A control circuitry 90 is connected to the plurality of switches 65. The control circuitry 90 is provided on, for example, the semiconductor substrate 601. The control circuitry 90 controls the plurality of switches 65. More specifically, the control circuitry 90 switches control schemes for the plurality of switches 65 in accordance with the standard cell mode and the high-resolution cell mode. In the standard cell mode, the control circuitry 90 controls the plurality of switches 65 so as to simultaneously read out electrical signals from the plurality of detector cells 61 belonging to each cell group 71 over a plurality of views, as shown in FIG. 6. In the high-resolution cell mode, the control circuitry 90 controls the plurality of switches 65 to read out electrical signals from the plurality of detector cells 61 belonging to each cell group 71 at different timings in each of a plurality of views, as shown in FIG. 7. In this manner, the control circuitry 90 controls the plurality of switches 65 for each cell group 71 so as to switch between the standard cell mode for almost simultaneously reading out electrical signals from the plurality of detector cells 61 belonging to each cell group 71 and the high-resolution mode for reading out electrical signals from the plurality of detector cells 61 belonging to each cell group 71 at different timings.

A control mode is uniformly set for all the cell groups 71 mounted on the X-ray detector 15. It is possible to arbitrarily set the control mode to the standard cell mode or the high-resolution cell mode via, for example, the input circuitry 41.

As shown in FIG. 8, more specifically, the control circuitry 90 includes the plurality of individual control circuits 554 and an overall control circuit 558. The plurality of individual control circuits 554 are provide by the same number as the number of the plurality of detector cells 61 constituting each cell group 71. For example, as shown in FIG. 8, assume that each cell group 71 includes four detector cells P1, P2, P3, and P4. In this case, four individual control circuits 554-1, 554-2, 554-3, and 554-4 are provided. Each individual control circuit 554 controls the switch 65 corresponding to a specific single detector cell of the plurality of detector cells 61 included in each of the plurality of cell groups 71. For example, the individual control circuit 554-1 controls the detector cell P1 of each cell group. The individual control circuit 554-2 controls the detector cell P2 of each cell group. The individual control circuit 554-3 controls the detector cell P3 of each cell group 71. The individual control circuit 554-4 controls the detector cell P4 of each cell group 71. Each individual control circuit 554 supplies switching signals to switches 65-4 of the plurality of cell groups 71 at connection destinations at almost the same timing.

The overall control circuit 558 controls the plurality of individual control circuits 554 to read out electrical signals from the plurality of detector cells P1, P2, P3, and P4 belonging to each of the plurality of cell groups 71. The overall control circuit 558 switches the control modes of the plurality of individual control circuits 554-1, 554-2, 554-3, and 554-4 in accordance with the standard cell mode and the high-resolution cell mode. The control mode is set in advance.

In the standard cell mode, the overall control circuit 558 controls the plurality of individual control circuits 554-1, 554-2, 554-3, and 554-4 so as to almost simultaneously read out electrical signals from the plurality of detector cells P1, P2, P3, and P4 belonging to each of the plurality of cell groups 71 over a plurality of views. That is, the plurality of individual control circuits 554-1, 554-2, 554-3, and 554-4 set in the standard cell mode almost simultaneously supply ON signals to a plurality of switches 65-1, 65-2, 65-3, and 65-4 at connection destinations. Upon receiving the ON signals, the switches 65-1, 65-2, 65-3, and 65-4 close connection. When connection is closed, electrical signals are almost simultaneously read out from the detector cells P1, P2, P3, and P4, and are supplied to the signal processing circuit 55 on the subsequent stage. In the standard cell mode, the connection of the switches 65-1, 65-2, 65-3, and 65-4 is not shut down. That is, in the standard cell mode, the detector cells P1, P2, P3, and P4 are always connected to the switches 65-1, 65-2, 65-3, and 65-4 over a plurality of views. This implements simultaneous readout of electrical signals, with each cell group 71 being regarded as standard cells.

In the high-resolution cell mode, the overall control circuit 558 controls the plurality of individual control circuits 554 so as to read out electrical signals from the detector cells P1, P2, P3, and P4 belonging to each of the plurality of cell groups 71 at different timings over a plurality of views. More specifically, the overall control circuit 558 supplies ON signals or OFF signals to the plurality of individual control circuits 554 at almost different timings over a plurality of views. Each individual control circuit 554 supplies a switching signal to the switch 65 at a connection destination in response to the supply of the control signal. More specifically, when the overall control circuit 558 issues an electrical signal readout start instruction, each of the individual control circuits 554-1, 554-2, 554-3, and 554-4 supplies an ON signal to a corresponding one of the switches 65-1, 65-2, 65-3, and 65-4 at connection destinations in each of a plurality of views. When the overall control circuit 558 issues an electrical signal readout end instruction, each individual control circuit supplies an OFF signal to a corresponding one of the switches 65-1, 65-2, 65-3, and 65-4 at the connection destinations in each of a plurality of views. Upon receiving the ON signals, the switches 65-1, 65-2, 65-3, and 65-4 at the connection destination close connection. When connection is closed, electrical signals are individually read out from the detector cells P1, P2, P3, and P4 at the connection destinations, and are supplied to the DAS elements 551 on the subsequent stage. Upon receiving the OFF signals, the switches 65-1, 65-2, 65-3, and 65-4 at the connection destinations shut down connection. When connection is shut down, electrical signals are accumulated in the detector cells P1, P2, P3, and P4. This implements sequential readout of electrical signals from the detector cells P1, P2, P3, and P4 for each cell group 71.

In the above arrangement, the overall control circuit 558 controls the plurality of switches 65 belonging to each cell group 71 via the individual control circuits 554. However, this embodiment is not limited to this. For example, the overall control circuit 558 may directly control the plurality of switches 65. That is, the overall control circuit 558 may be directly connected to the plurality of switches 65 without via the individual control circuits 554. In this case, the overall control circuit 558 controls the plurality of switches 65 for each cell group 71 so as to switch between the standard cell mode for almost simultaneously reading out electrical signals from the plurality of detector cells 61 belonging to each cell group 71 and the high-resolution mode for reading out electrical signals from the plurality of detector cells 61 belonging to each cell group 71 at different timings.

Note that the above description is based on the assumption that one control circuit 90 is provided for all the detector cells included in the X-ray detector 15. However, this embodiment is not limited to this. Note that a plurality of control circuits 90 may be dispersed on a plurality of detector cell chips. In this case, the individual control circuits 554 of each control circuit 90 control detector cells belonging to each cell group 71 arranged near the control circuit 90. This can improve the independence of each detector cell chip.

In the above description, a control mode is uniformly set for the plurality of cell groups 71 in advance. However, this embodiment is not limited to this. For example, the control circuit 90 may uniformly switch, for the plurality of cell groups 71, between the standard cell mode and the high-resolution cell mode during CT imaging (i.e., during the rotation of the rotating frame 11). For example, when performing helical scanning, it is preferable to set the high-resolution cell mode during scanning on a region which requires a high-resolution, such as the lungs, and set the standard cell mode during scanning on a region which does not require a high resolution, such as the abdomen. In addition, when performing ECG-gated scanning, it is preferable to set the high-resolution cell mode during a period in which a high resolution is required and set the standard cell mode in which a low dose is required.

In addition, the control circuitry 90 may set the control mode for each cell group 71 to the standard cell mode or the high-resolution cell mode depending on the location of the X-ray detector 15. For example, raw data from the detector cells 61 located at end portions of the X-ray detector 15 in the channel direction do not contribute to an image as compared with raw data from the detector cells 61 located at a central portion. The control circuitry 90 therefore preferably sets the standard cell mode for the cell groups 71 located at the end portions in the channel direction, and sets the high-resolution cell mode for the cell groups 71 located at the central portion in the channel direction. This makes it possible to perform data acquisition at the central portion, which relatively contributes to image, in the high-resolution cell mode, and to perform data acquisition at the end portions, which relatively do not contribute to an image, in the standard cell mode. This can reduce the data amount while maintaining the resolution as compared with when all data acquisition is performed in the high-resolution cell mode, and can increase the resolution as compared when all data acquisition is performed in the standard cell mode. Alternatively, optimal circuitry design for the standard cell mode, i.e., circuitry design for the simultaneous readout scheme, may be made for the cell groups 71 located at the end portions in the channel direction, and optimal circuitry design for the high-resolution cell mode, i.e., circuitry design for the sequential readout scheme, may be made for the cell groups 71 located at the central portion. In other words, only a plurality of detector cells located at the central portion in the channel direction may be provided with the circuitry design unique to this embodiment as shown in FIG. 4, that is, may be divided into the plurality of cell groups 71. This can simplify circuitry design for the end portions in the channel direction. Note that analog bundling may be performed for the plurality of detector cells 61 belonging to the cell groups 71 in the simultaneous readout scheme. That is, the plurality of detector cells 61 may be connected to the signal switch 65 via a common signal wiring line. This can reduce the number of switches 65, and hence can reduce the manufacturing cost and facilitate control of the switches 65.

The structure of the X-ray detector 15 according to this embodiment will be described in detail next. For the sake of a concrete description, assume that the detector cells 61 are photodiodes. The structures of X-ray detectors 15 according to this embodiment are broadly classified into a type using front-illuminated type photodiodes and a type using back-illuminated type photodiodes.

Figure 9:
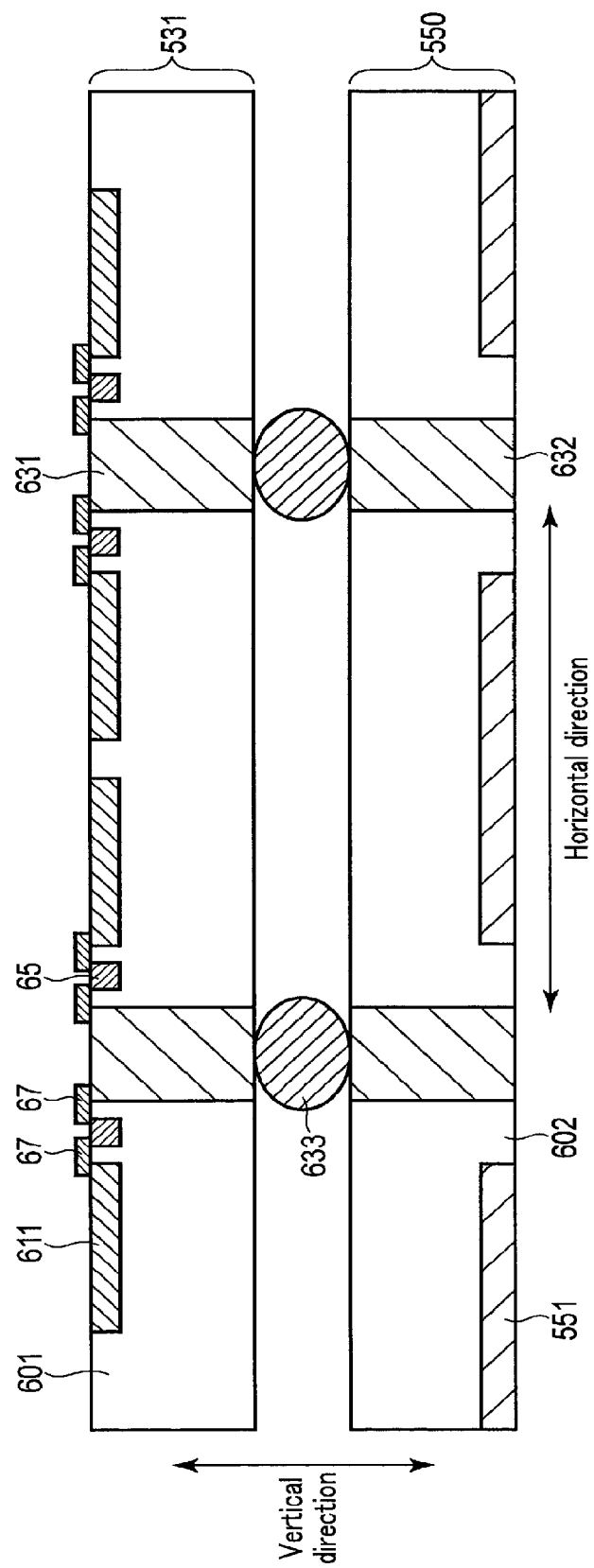
FIG. 9 is a view showing a detailed partial arrangement of the X-ray detector using front-illuminated type photodiodes according to this embodiment.

FIG. 9 is a view showing a detailed partial arrangement of the X-ray detector 15 using front-illuminated type photodiodes according to this embodiment. FIG. 9 is a sectional view of a detector cell chip 531 and a DAS chip 550 included in the X-ray detector 15. As shown in FIG. 9, the front-illuminated type detector cell chip 531 includes the semiconductor substrate 601. A plurality of photodiode anodes 611 are formed in the surface of the semiconductor substrate 601. First through electrodes 631 are formed between the plurality of photodiode anodes 611 in the semiconductor substrate 601. The first through electrodes 631 are parts of the through electrodes 63 described above. Each first through electrode 631 is formed by forming a metal film on the inner circumferential surface of a through hole formed in the semiconductor substrate 601. As described above, each first through electrode 631 is formed in almost the central portion of the anodes 611 of the plurality of detector cells constituting each cell group. The switch 65 is provided between each photodiode anodes 611 and the corresponding first through electrode 631, and the anode 611, the switch 65, and the first through electrode 631 are connected to each other via the signal wiring lines 67. The DAS chip 551 is provided on the back surface of the detector cell chip 531. The DAS chip 550 includes a semiconductor substrate 602. The plurality of DAS elements 551 are provided on the back surface of the semiconductor substrate 602.

Each DAS element 551 is an integrated circuit formed by a semiconductor technique such as ASIC. In addition, second through electrodes 632 are formed between the plurality of DAS elements 551 on the semiconductor substrate 602. The second through electrodes 632 are connected to the DAS elements 551 via signal wiring lines (not shown). Each second through electrode 632 is formed by forming a metal film on the inner circumferential surface of a through hole formed in the semiconductor substrate 602. The first through electrode 631 and the second through electrode 632 constitute the through electrode 63 described above. The first through electrodes 631 are connected one-to-one to the second through electrodes 632 via bumps 633. The anodes 611 and the DAS elements 551 are connected to each other via the signal wiring lines 67, the switches 65, the first through electrodes 631, the bumps 633, and the second through electrodes 632. Although the first through electrodes 631 are connected to the second through electrodes 632 via the bumps 633, this is not exhaustive, and they may be connected by any method. One DAS element 551 is provided for each cell group.

Figure 10:
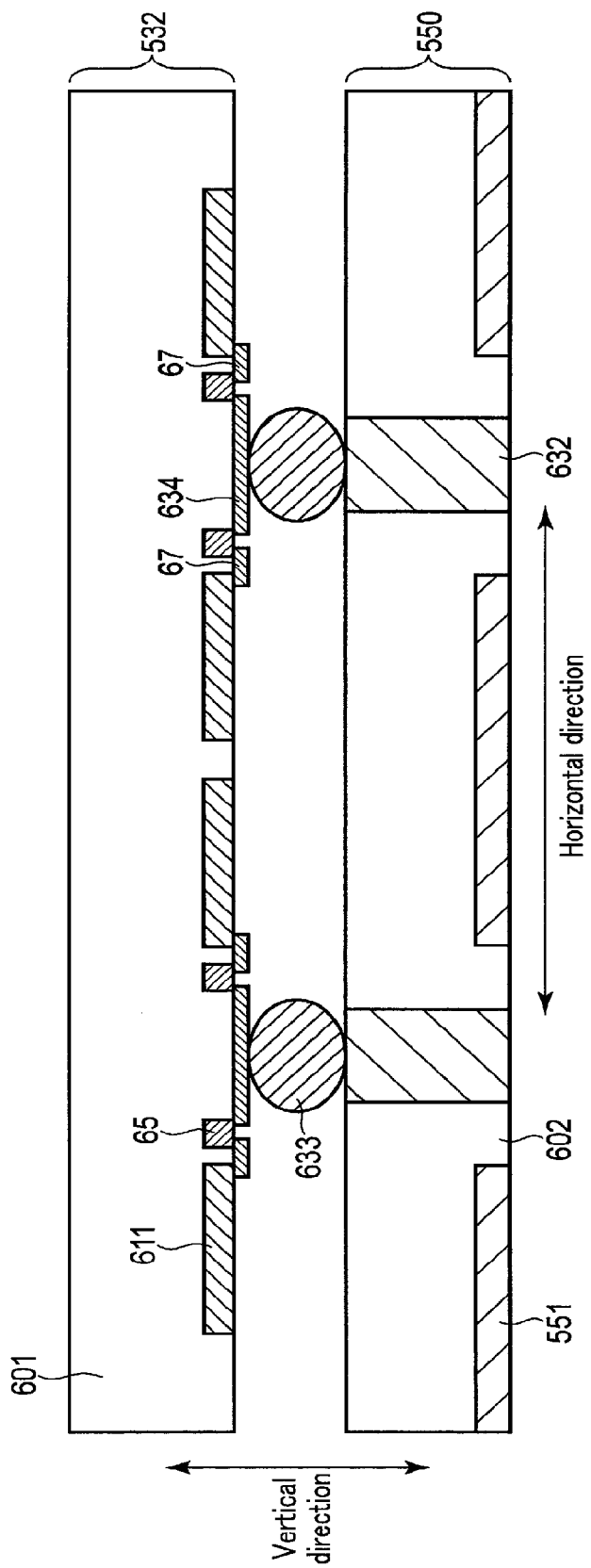
FIG. 10 is a view showing a detailed partial arrangement of the X-ray detector using back-illuminated type photodiodes according to this embodiment.

FIG. 10 is a view showing a detailed partial arrangement of the X-ray detector 15 using back-illuminated type photodiodes according to this embodiment. As shown in FIG. 10, the plurality of electrodes 611 are formed in the back surface of the semiconductor substrate 601 of the back-illuminated type detector cell chip 531. Conductors 634 are formed between the plurality of electrodes 611 on the semiconductor substrate 601. The switches 65 are provided between the electrodes 611 and the conductors 634. The electrodes 611, the switches 65, and the conductors 634 are connected via the signal wiring lines 67. The DAS chip 550 is provided on the back surface of the detector cell chip 531. The conductors 634 are connected to the second through electrodes 632 via the bumps 633. In this manner, the electrodes 611 are connected to the DAS chips 550 via the signal wiring lines 67, the switches 65, the conductors 634, the bumps 633, and the second through electrodes 632. Note that the conductors 634 are connected to the second through electrodes 632 via the bumps 633. However, this is not exhaustive, and they may be connected by any method.

This is the end of the description of the detail structure of the X-ray detector 15.

Figure 11:
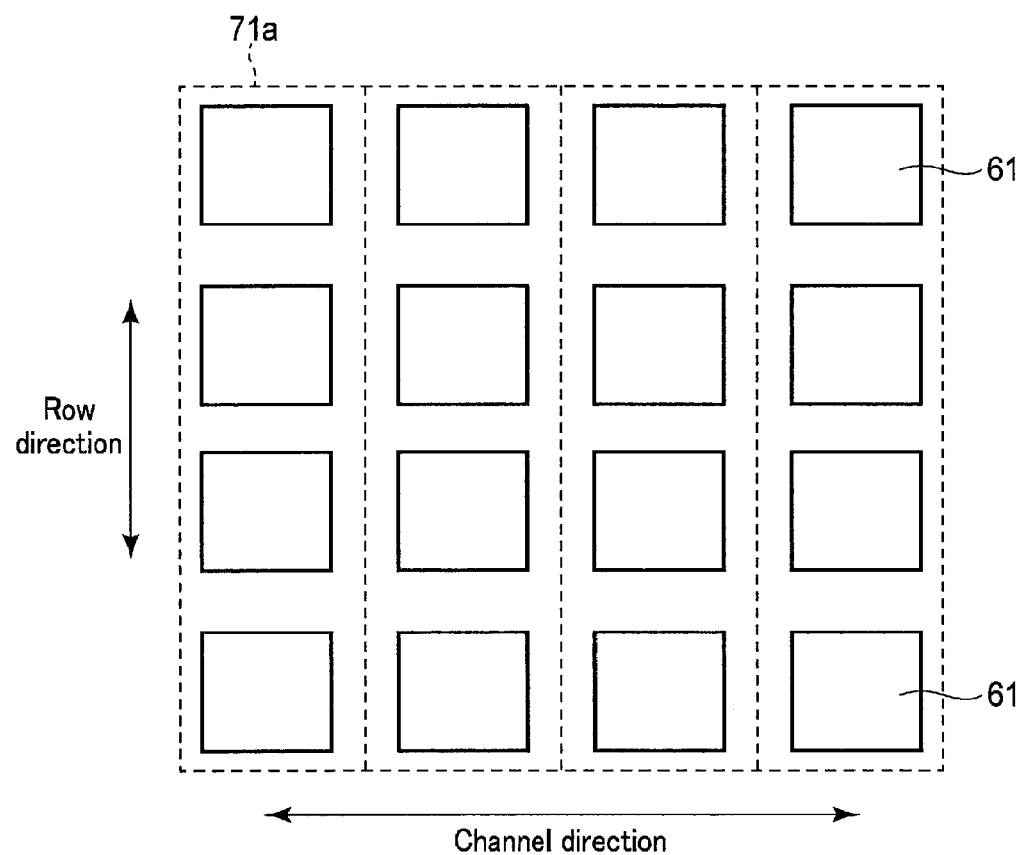
FIG. 11 is a view showing another example of a cell group according to this embodiment.

Note that in the above description, the number of cells included in each cell group 71 in the row direction is the same as that in the channel direction. Adopting such square cell groups can unify the aspect ratios of cells in the high-resolution cell mode and the standard cell mode. However, this embodiment is not limited to this. More specifically, as shown in FIG. 11, the number of cells in the row direction may be larger than that in the channel direction. For example, the numbers of cells in the column and channel directions may be respectively set to four and two, or the numbers of cells in the column and channel directions may be respectively set to two and one. In addition, as shown in FIG. 12, the number of cells in the row direction may be larger than that in the channel direction. For example, the numbers of cells in the column and channel directions may be respectively set to two and four, or the numbers of cells in the column and channel directions may be respectively set to one and two.

As described above, the X-ray computed tomography apparatus according to this embodiment includes the X-ray tube 13, the plurality of detector cells 61, the plurality of switches 65, the plurality of DAS elements 551, the control circuitry 90, and the reconstruction circuitry 33. The X-ray tube 13 generates X-rays. The plurality of detector cells 61 are provided on the semiconductor substrate 60 and detect X-rays, and are divided into the plurality of cell groups 71. The plurality of switches 65 are respectively connected to the plurality of detector cells 61. The plurality of DAS elements 551 are respectively connected to the plurality of cell groups 71 and integrate electrical signals from the plurality of detector cells 61 belonging to each cell group 71. The control circuitry 90 controls the plurality of switches 65 for each cell group 71 so as to switch between the first connection for almost simultaneously reading out electrical signals from the plurality of detector cells 61 belonging to each cell group 71 and the second connection for reading out electrical signals from the plurality of detector cells 61 belonging to each cell group 71 at different timings. The reconstruction circuitry 33 reconstructs an image based on outputs from the plurality of DAS elements 551.

From another point of view, the X-ray computed tomography apparatus according to this embodiment includes the X-ray detector 15. The X-ray detector 15 includes the semiconductor substrate 60, the plurality of detector cells 61, the plurality of through electrodes 63, and the signal processing circuitry 55. The plurality of detector cells 61 are provided on the semiconductor substrate 60 and detect X-rays. The plurality of detector cells 61 are divided into the cell groups 71 smaller in number than the cells. The plurality of through electrodes 63 are provided in the semiconductor substrate 60 between the plurality of detector cells 61, and are smaller in number than the detector cells 61. Each through electrode 63 is connected to the plurality of detector cells 61, of the plurality of detector cells 61, which belong to each cell group via the signal wiring lines 67. The signal processing circuitry 55 processes electrical signals supplied from the plurality of detector cells 61 via the plurality of through electrodes 63.

With the above arrangement, the X-ray detector 15 according to this embodiment includes the circuitry arrangement which is formed by bundling the plurality of detector cells 61 into the cell groups 71 on a standard cell basis and can implement both the standard cell mode of performing data acquisition with a standard resolution and the high-resolution cell mode of performing data acquisition with a high resolution. In the standard cell mode, each cell group 71 is regarded as a standard cell, and data acquisition is performed in the simultaneous readout mode. That is, in the standard cell mode, the X-ray detector 15 almost simultaneously reads out electrical signals from the plurality of detector cells 61 belonging to the cell group cell group 71. Unlike the related art, since the through electrodes 63 are provided between the detector cells 61, an effective cell areas can also be ensured even in the standard cell mode of performing simultaneous readout.

In addition, since the signal wiring lines 67 are bundled for each cell group 71, it is possible to implement simultaneous readout without the high density of the signal wiring lines 67. Furthermore, in the high-resolution cell mode, the X-ray detector 15 performs data acquisition by the sequential readout scheme for each detector cell 61 which is a high-resolution cell. That is, in the high-resolution cell mode, the X-ray detector 15 reads out electrical signals from the plurality of detector cells 61 belonging to each cell group 71 at different timings. Setting each cell group 71 as one unit of sequential readout can reduce the collapse of simultaneity in terms of integration time as compared with the related art which sets each column as one unit of sequential readout.

It is therefore possible to provide an X-ray detector and an X-ray computed tomography apparatus which can perform both data acquisition with a standard resolution and data acquisition with a high resolution.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray computed tomography apparatus comprising:
an X-ray tube configured to generate X-rays;
a plurality of detector cells provided on a substrate, divided into a plurality of groups, and configured to detect the X-rays;
a plurality of switches respectively connected to the plurality of detector cells;
a plurality of data acquisition elements respectively connected to the plurality of groups and configured to integrate electrical signals from a plurality of detector cells belonging to each of the groups;
a control circuitry configured to control the plurality of switches for each of the groups so as to switch between first connection for substantially simultaneously reading out electrical signals from a plurality of detector cells belonging to each of the groups and second connection for reading out electrical signals from a plurality of detector cells belonging to each of the groups at different timings; and
a reconstruction circuitry configured to reconstruct an image based on outputs from the plurality of data acquisition elements.

2. The apparatus of claim 1, further comprising a plurality of through electrodes which are provided in the substrate between the plurality of detector cells and are smaller in number than the plurality of detector cells,
the through electrodes being respectively connected to a plurality of detector cells belonging to each of the groups via wiring lines.

3. The apparatus of claim 2, wherein the substrate includes a first substrate and a second substrate provided on a back side of the first substrate,
each of the plurality of through electrodes includes a first through electrode provided in the first substrate and a second through electrode provided in the second substrate,
the plurality of detector cells are provided on an front surface of the first substrate,
The plurality of data acquisition elements are provided on a back surface of the second substrate, and
the first through electrodes and the second through electrodes are connected to each other via bumps.

4. The apparatus of claim 2, wherein the substrate includes a first substrate and a second substrate provided on a back side of the first substrate,
the plurality of through electrodes are provided on the second substrate,
the plurality of detector cells are provided on a back surface of the first substrate,
conductors are provided between a plurality of detector cells belonging to each of the groups,
the plurality of data acquisition elements are provided on a back surface of the second substrate, and
the conductors and the through electrodes are connected to each other via bumps.

5. The apparatus of claim 2, wherein each of the through electrodes is provided in substantially the center of a plurality of detector cells belonging to each of the groups on the substrate.

6. The apparatus of claim 1, wherein a cell count of each of the groups in a row direction is equal to a cell count in a channel direction.

7. The apparatus of claim 1, wherein a cell count of each of the groups in a row direction is larger than a cell count in a channel direction.

8. The apparatus of claim 1, wherein a cell count of each of the groups in a row direction is smaller than a cell count in a channel direction.

9. The apparatus of claim 1, wherein groups, of the plurality of groups, which are used for the first connection are provided at end portions in a channel direction, and groups, of the plurality of groups, which are used for the second connection are provided at a central portion in the channel direction.

10. The apparatus of claim 9, wherein a plurality of detector cells belonging to a group for the first connection are connected to a single switch via a common wiring line.

11. The apparatus of claim 1, wherein the control circuitry switches between the first connection and the second connection with respect to each of the plurality of groups during CT imaging.

12. The apparatus of claim 1, wherein the control circuitry include a plurality of individual control circuits corresponding to a cell count of each of the groups and an overall control circuit configured to control the plurality of individual control circuits,
each of the individual control circuits controls ON/OFF operation of a control target switch of a plurality of switches belonging to each of the groups, and
the overall control circuit controls the plurality of individual control circuits so as to read out electrical signals from a plurality of detector cells belonging to each of the groups at a predetermined timing.

13. An X-ray detector comprising:
a plurality of detector cells provided on a substrate, divided into a plurality of groups, and configured to detect X-rays;
a plurality of switches respectively connected to the plurality of detector cells;
a plurality of data acquisition elements respectively connected to the plurality of groups and configured to integrate electrical signals from a plurality of detector cells belonging to each of the groups; and
a control circuitry configured to control the plurality of switches for each of the groups so as to switch between first connection for substantially simultaneously reading out electrical signals from a plurality of detector cells belonging to each of the groups and second connection for reading out electrical signals from a plurality of detector cells belonging to each of the groups at different timings.

* * * * *